United States Patent [19]

Lerman

[11] Patent Number: 4,607,629
[45] Date of Patent: Aug. 26, 1986

[54] DYNAMIC POST-OPERATIVE HIP ABDUCTION BRACE

[76] Inventor: Max Lerman, 1950 Carla Ridge, Beverly Hills, Calif. 90210

[21] Appl. No.: 715,061

[22] Filed: Mar. 21, 1985

[51] Int. Cl.$^4$ .............................................. A61F 5/00
[52] U.S. Cl. ................................ 128/80 A; 128/87 C
[58] Field of Search ................ 128/80 A, 87 C, 80 R, 128/80 B, 80 J

[56] References Cited

U.S. PATENT DOCUMENTS

| | | | |
|---|---|---|---|
| 2,632,439 | 3/1953 | Hickerson | 128/80 |
| 2,690,176 | 9/1954 | Nelson | 128/80 |
| 3,068,862 | 12/1962 | Fuzere | 128/87 C |
| 3,228,399 | 1/1966 | Riedell | 128/303 |
| 3,910,267 | 10/1975 | Reiman | 128/80 A |
| 3,973,559 | 8/1976 | Reiman | 128/80 A |

OTHER PUBLICATIONS

Advertisement of Richards, "Pehr Abduction Hip Splint", Journal of Bone & Joint Surgery, vol. 47-A, No. 2, p. 81, Mar. 1965.

Primary Examiner—Clifford D. Crowder
Attorney, Agent, or Firm—Christie, Parker & Hale

[57] ABSTRACT

A dynamic post-operative hip abduction brace comprises a pair of spaced apart U-shaped cuffs adapted for attachment to the insides of the upper legs of a patient, and a generally inverted U-shaped supporting bridge secured between the leg-supporting cuffs. The bridge comprises a generally planar unitary piece made from a semi-rigid material. The bridge member has a cross-member extending between the cuffs and a pair of spaced apart leg members diverging downwardly away from the cross-member of the bridge. The leg members of the bridge are rigidly secured to inside faces of the cuffs for holding the cuffs at a fixed abduction angle set by the diverging leg members of the bridge. The cross-member and leg members of the bridge are each of U-shaped channel configuration. The bridge has sufficient rigidity to hold the cuffs at the fixed abduction angle during use, while permitting sufficient bending of either leg member of the bridge about either of the ends of the bridge cross-member to permit the patient wearing the brace to walk with a normal gait soon after hip surgery.

8 Claims, 4 Drawing Figures

DYNAMIC POST-OPERATIVE HIP ABDUCTION BRACE

FIELD OF THE INVENTION

This invention relates to orthopedic devices, and more particularly to a hip abduction brace designed for post-operative use to permit early ambulation following hip surgery.

BACKGROUND OF THE INVENTION

After hip surgery, a hip abduction brace is commonly worn to hold the upper legs of the patient at a fixed abduction angle during the rehabilitation period. The abduction angle is the angle between the axis of the upper leg and a vertical centerline between the legs. The brace is worn to prevent the upper legs from moving toward each other. By holding the legs at an abduction angle of about 15° to 20° during rehabilitation, hip dislocation can be prevented.

A brace, known as the Pehr hip abduction splint, has been used in the past to satisfy the need for a post-operative brace for holding the legs of a patient at a desired abduction angle following hip surgery. The Pehr hip abduction splint includes a pair of large U-shaped cuffs adapted for attachment to the insides of the patient's upper legs, and a complex rigid spreader mechanism secured between the cuffs. The spreader mechanism includes a vertically extending threaded shaft carried on a metal plate to which two pairs of pivot arms are attached. Rotation of the shaft pivots the two pairs of arms to adjust the amount of spacing between the cuffs. This permits adjustment of the brace to match patient size. The spreader mechanism is rotatably secured to each cuff so that the cuffs can swing through a small abduction angle. Neither cuff can rotate through an angle perpendicular to the plane of the spreader mechanism. The Pehr hip abduction splint is useful in maintaining a hip abduction angle for patients of various sizes, but the splint has a number of disadvantages overcome by the present invention. The Pehr splint is expensive primarily because of the complex multi-component spreader mechanism. It also adds to the weight of the splint. In addition, the rigidity of the splint prevents the patient from walking during the post-operative period. Therefore, the brace inhibits early ambulation and use in transferring patients following hip surgery.

SUMMARY OF THE INVENTION

Briefly, this invention provides a dynamic post-operative hip abduction brace which is simple to manufacture, light in weight and inexpensive. It is also effective in holding the patient's legs at a required abduction angle while permitting a controlled reciprocating gait in hip abduction that permits early ambulation following hip surgery.

In one embodiment of the invention, the hip abduction brace comprises a pair of laterally spaced apart U-shaped cuffs adapted for attachment to the insides of the legs above the knees. An inverted U-shaped, generally planar bridge made from a semi-rigid material is secured between the leg-supporting cuffs. The bridge comprises a unitary piece having an elongated cross-member extending between the cuffs, and a pair of spaced apart leg members diverging away from the cross-member of the supporting bridge. The leg members of the bridge are rigidly affixed to the cuffs below the cross-member for holding the legs of the patient at a fixed abduction angle. The cross-member of the bridge is substantially rigid longitudinally to maintain a fixed spacing between the cuffs at opposite ends of the cross-member. The leg members are sufficiently rigid to maintain the fixed spacing at the set abduction angle. Each leg member of the bridge is bendable about the end of the cross-member in a direction generally perpendicular to the plane of the bridge. This permits a normal walking gait for the user wearing the brace.

These and other aspects of the invention will be more fully understood by referring to the following detailed description and the accompanying drawings.

DRAWINGS

DETAILED DESCRIPTION

Figure 1:
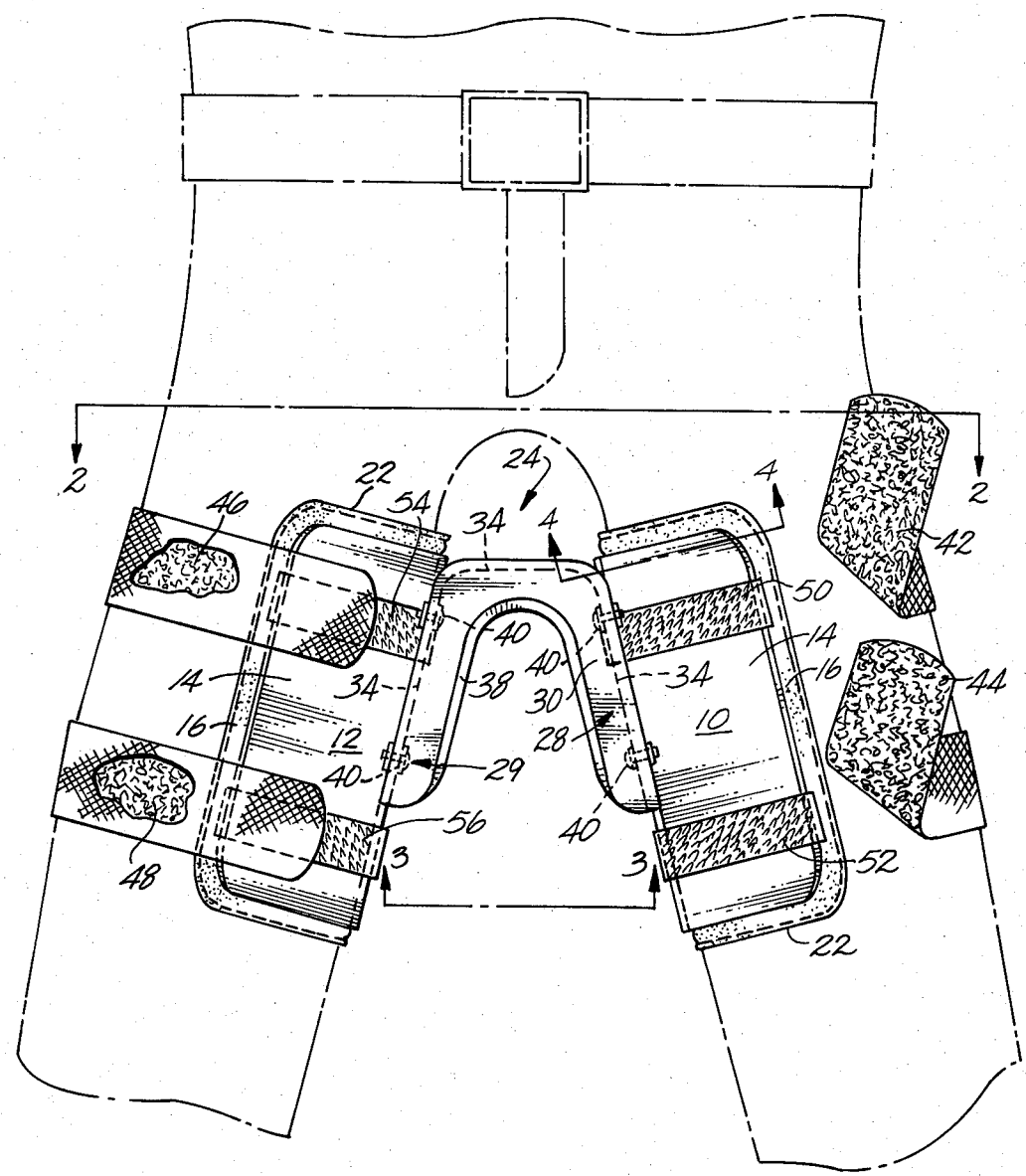
FIG. 1 is a front elevation view showing a dynamic post-operative hip abduction brace according to principles of this invention.
Figure 2:
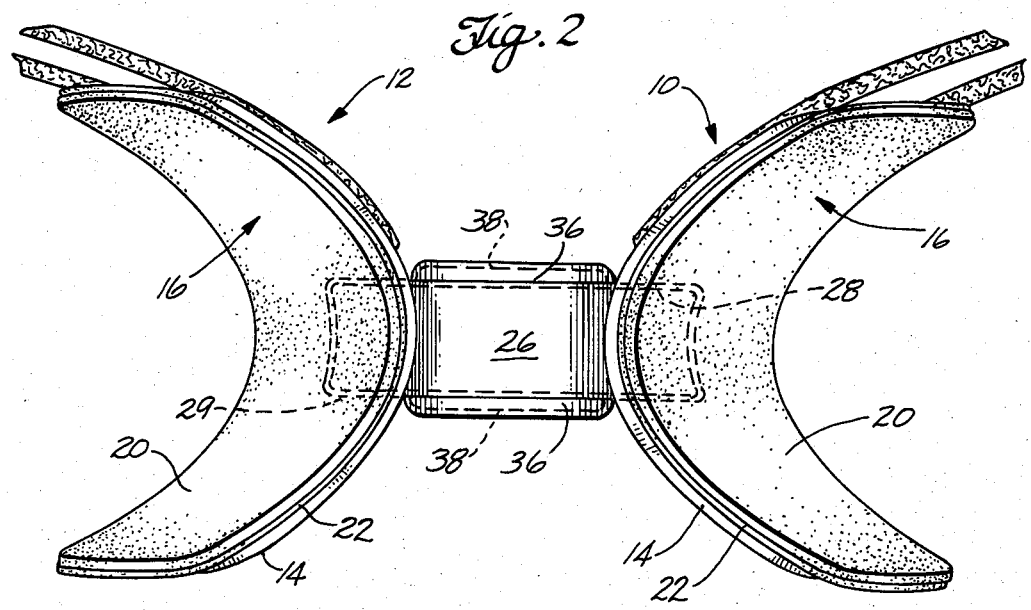
FIG. 2 is a top view of the brace taken on line 2—2 of FIG. 1.

Referring to the drawings, a dynamic post-operative hip abduction brace includes a left cuff 10 and a right cuff 12 for overlying the inside regions of the left and right upper legs, respectively. Each cuff comprises an elongated U-shaped semi-rigid leg support member 14 which is relatively thin and of uniform wall thickness. The U-shaped leg support members 14 are spaced apart so that the bight portions of the U's are closest to one another with the U-shaped support members opening outwardly away from each other.

The inside face of each U-shaped leg support member includes a layer of soft, resiliently compressible padding 16 which preferably includes an interior layer of a resilient plastic foam material, preferably an open cell foam such as polyethylene or polyurethane foam 18. The foam layer is enclosed within an outer layer of a flexible, soft open cell fabric such as velour 20. The velour outer layer is secured around the exterior of the inner foam layer by peripheral stitching 22. The semi-rigid U-shaped walls 14 of the cuffs are preferably made from a lightweight plastic material having good rigidity with a modest amount of lateral flexibility. The U-shaped cuffs are rigid longitudinally. Polypropylene is a desired material. In the illustrated embodiment, the semi-rigid U-shaped leg-supporting members 14 are approximately eight inches in height with a uniform wall thickness of about 3/16 to ¼ inch.

An inverted U-shaped bridge member 24 is rigidly secured between the two cuffs for holding the cuffs at a desired abduction angle. The bridge member has a base portion or cross-member 26 extending horizontally between upper portions of the cuffs. Downwardly and outwardly diverging left and right leg portions 28 and 29 of the bridge are rigidly affixed to the bight portions of the left and right cuffs below the cross-member 26 of the bridge. The diverging leg portions of the bridge member lie in a common plane with the bridge cross-member 26. The leg members of the bridge hold the cuffs at an abduction angle of about 15° to 20°. This angle is measured between the inside edge of each cuff (or the outside edge of each bridge leg member) and a vertical centerline between the two cuffs.

The bridge member is a unitary piece made from a semi-rigid plastic material. The cross-member and leg portions of the bridge member have a cross section of U-shaped channel configuration. The channel-shaped cross section is continuous from one end of the U to the other. The cross-member and leg portions of the bridge member thus have a continuous inverted U-shaped front wall 30, a continuous inverted U-shaped rear wall 32 spaced to the rear of and extending parallel to the front wall 30, and a web 34 of uniform width formed integrally with the front and rear walls of the bridge member. The width of the front and rear walls of the bridge member is about ¾ to 1 inch. The wall thickness of the web 34 and the front and rear walls 30 and 32 is between about 3/16 to ¼ inch. The channel-shaped cross section of the cross-member and leg portions of the bridge add substantial stiffness (both axial stiffness and lateral stiffness) to these portions of the bridge.

A separate flange 36 is formed along the inverted U-shaped inside edge of the front and rear walls of the bridge member. Each flange projects outwardly from the face of its corresponding wall, and a lip 38 is formed integrally along the edge of each flange. These flanged portions add strength to the front and rear walls of the bridge member.

The inverted U-shaped bridge member is preferably made from a single piece of semi-rigid plastic material, and the entire bridge member is formed as a unit preferably by vacuum forming techniques. A preferred material is polypropylene.

Figure 3:
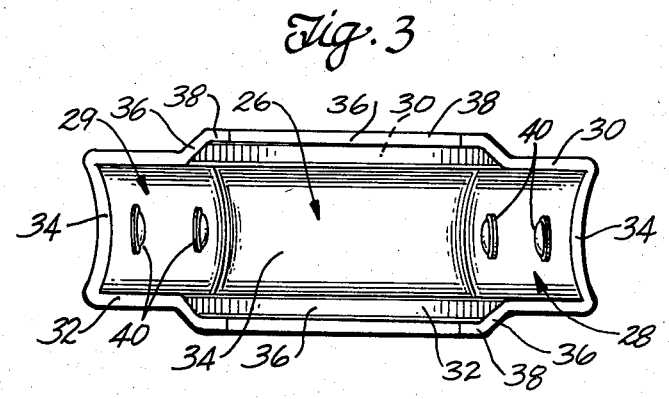
FIG. 3 is a bottom view of the brace taken on line 3—3 of FIG. 1.
Figure 4:
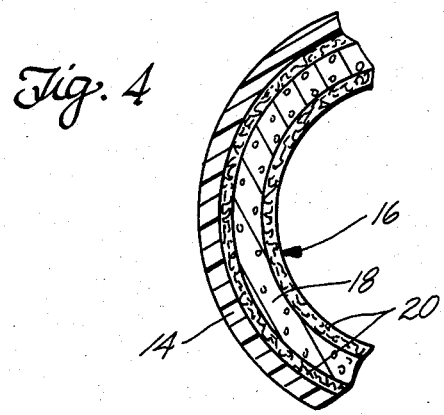
FIG. 4 is a cross section taken on line 4—4 of FIG. 1.

Preferably, the web portions 34 of the left and right legs 28 and 29 of the bridge member are formed with a concave curvature to match the curvature of the bight portions of the cuffs to which the leg portions of the bridge member are attached. This curvature is best illustrated in FIG. 3. A separate pair of vertically spaced apart fasteners 40 rigidly affix the web portions of the right and left legs of the bridge member to the adjacent bight portions of the cuffs. The fasteners maintain the leg portions 28 and 29 of the bridge member in a rigid immovable position with respect to the cuffs.

The hip abduction brace is worn by placing the left and right cuffs 10 and 12 against the insides of the left and right upper legs. The cuffs extend for most of the length of the upper leg, from a short distance below the crotch to a short distance above the knees. Each cuff is then tightly fastened around the upper legs by fastening means which includes flexible upper and lower left straps 42 and 44 secured to the left cuff and flexible upper and lower right straps 46 and 48 secured to the right cuff. Although a variety of fastening means can be used, it is preferable to fasten the straps to the cuffs by cooperating thistle cloth fasteners. In the illustrated embodiment, the straps are made of a nylon fabric and the inside face of each of the straps on each cuff has a Velcro-type pile material, each adapted for fastening to a corresponding length of a Velcro-type hook material secured to the cuffs. As shown best in FIG. 1, parallel upper and lower fasteners 50 and 52 of a Velcro-type hook material are secured to the inside face of the left cuff on a side of the cuff opposite from the padded inside face. Similarly, vertically spaced apart parallel fasteners 54 and 56 comprising lengths of a Velcro-type hook material are similarly secured to the inside face of the left cuff. The fastener portions of the upper and lower left straps are releasably attached to the upper and lower fasteners 50 and 52 on the left cuff so that these straps can extend around the circumference of the left leg. The ends of the left straps are attached to the upper and lower fasteners 50 and 52 on the cuff for holding the left cuff on the left upper leg. Similarly, the right straps 46 and 48 are extended around the right upper leg and then attached to portions of the upper and lower right fasteners 54 and 56 on the right cuff for holding the brace in place between the right and left upper legs.

With the brace secured to the patient's upper legs, the inverted U-shaped bridge extends between the legs of the patient to hold the legs in a fixed position at the abduction angle set by the diverging outer legs 28 and 29 of the inverted U-shaped bridge member. The leg portions 28 and 29 of the bridge member have sufficient rigidity to hold the legs of the patient in a fixed position, at the set abduction angle, during use of the brace. This inhibits inward movement of the patient's legs toward each other and holds the patient's legs at the set abduction angle while the brace is worn, including during walking. The channel-shaped cross-member 26 of the bridge has substantial longitudinal rigidity. The portions of the cuffs attached near the ends of the cross-member portion of the bridge are prevented from being spread apart or moved closer together by the rigidity of the axially stiff cross-member 26. It is this stiffness provided by the bridge cross-member that is principally responsible for preventing inward movement of the patient's legs during use of the brace. The leg portions 28 and 29 of the bridge also have sufficient lateral rigidity to resist relative inward movement of the two cuffs to hold the legs of the patient at the set abduction angle. The leg portions of the bridge resist inward movement of the patient's legs with a resistance force sufficient to prevent hip dislocation following hip surgery.

The semi-rigid material from which the bridge member is constructed permits a controlled amount of flexing of the leg portions of the bridge during use. Although the cross-member 26 is essentially rigid axially, it is torsionally flexible and capable of twisting from a force applied to either end of the bridge cross-member, from either of the leg portions of the bridge, in a direction perpendicular to the plane of the bridge. This capability of bending in torsion allows the patient wearing the brace to walk with a normal gait while the legs are maintained at the fixed abduction angle. That is, during forward or rear rotation of either bridge leg member 28 or 29 in a direction perpendicular to the plane of the bridge, the semi-rigid material from which the bridge member is constructed allows the ends of the bridge cross-member 26 to twist sufficiently to permit reciprocating motion of either leg portion of the bridge relative to the bridge cross-member. The ends of the bridge cross-member are rigidly affixed to the cuffs, and leverage from the normal walking gait is applied to the leg portions of the bridge member. This causes the semi-rigid material at the ends of the bridge cross-member to flex sufficiently to accommodate the walking motion in a controlled manner. Reciprocal motion is not unrestrained, for example, because of the force required to bend the leg portions of the semi-rigid bridge member. This resistance force causes the patient to walk with a deliberate walking gait. The semi-rigid material from which the brace is made also is sufficiently resilient to permit either leg portion of the bridge which has been twisted relative to the bridge cross-member to return to its normal position when the reciprocal force is released. This also assists in allowing walking with a controlled deliberate reciprocal gait.

Thus, the invention provides a lightweight dynamic hip abduction brace which a patient can wear after hip surgery to hold the legs of the patient at the desired abduction angle during rehabilitation. The brace is inexpensive and requires no moving parts. It also allows reciprocation of the legs with a normal walking gait so that the patient can begin the rehabilitation process sooner than with a brace too stiff to allow the patient to walk naturally. As a result, the patient can become rehabilitated sooner and can also be transferred within the hospital more easily.

What is claimed is:

1. A dynamic hip abduction brace comprising:
   a pair of laterally spaced apart U-shaped cuffs adapted for attachment to the inside regions of legs above the knees;
   a generally inverted U-shaped supporting bridge secured between the leg-supporting cuffs and comprising a unitary piece having a cross-member extending between the leg-supporting cuffs, and a pair of spaced apart outwardly diverging leg portions formed integrally with and extending away from the cross-member of the supporting bridge; and
   means rigidly affixing the leg portions of the bridge to the leg-supporting cuffs so that each leg member is substantially immovable relative to its corresponding cuff for holding the legs at a fixed abduction angle; the unitary bridge member being made from a semi-rigid material such that the cross-member of the bridge is substantially rigid longitudinally to maintain the cuffs in a rigidly fixed spaced apart position for maintaining a fixed spacing between the legs of a patient, while each leg portion of the bridge is bendable in a direction generally perpendicular to the plane of the bridge member so that each leg member and its corresponding cuff can be rotated forward or backward at the end of the bridge cross-member to permit a normal walking gait.

2. Apparatus according to claim 1 in which the cross-member and leg portions of the bridge member are all of U-shaped channel configuration.

3. Apparatus according to claim 2 in which the channel forms front and rear faces of the bridge member, and the front and rear faces have an inverted U-shaped inside edge; and including a flange extending along the inside edge of the front and rear face of the bridge member for adding structural rigidity to the cross-member and leg portions of the bridge.

4. Apparatus according to claim 1 in which the semi-rigid material has sufficient resiliency to return either leg member to its normal position after an inward force on either leg member in the plane of the bridge is released.

5. A dynamic hip abduction brace comprising:
   a pair of spaced apart U-shaped cuffs adapted for attachment to inside regions of the legs above the knees;
   a generally inverted U-shaped supporting bridge secured between the leg-supporting cuffs and comprising a unitary piece having a cross-member extending between the leg-supporting cuffs, and a pair of spaced apart outwardly diverging leg portions extending away from the cross-member of the bridge; and
   means rigidly affixing the leg portions of the bridge to the leg-supporting cuffs for holding the cuffs at a fixed abduction angle; the unitary bridge member being made from a semi-rigid material so that the cross-member of the bridge is substantially rigid longitudinally for holding the cuffs at its opposite ends in a fixed spaced apart position, the union of the leg portions with the ends of the cross-member being sufficiently bendable to permit reciprocating motion of either leg portion in a direction generally perpendicular to the plane of the bridge cross-member for allowing the legs of a user to rotate with a normal walking gait while maintaining the legs of the user at the fixed abduction angle.

6. Apparatus according to claim 5 in which the cross-member and leg portions of the bridge member are all of U-shaped channel configuration.

7. Apparatus according to claim 6 in which the channel forms front and rear faces of the bridge member; and the front and rear faces have an inverted U-shaped inside edge; and including a flange extending along the inside edge of the front and rear face of the bridge member for adding structural rigidity to the cross-member and leg portions of the bridge.

8. Apparatus according to claim 5 in which the semi-rigid material is sufficiently resilient to return to its normal position after either leg portion of the bridge has been bent under a reciprocating force experienced during a normal walking motion of a patient wearing the brace.

* * * * *